(12) United States Patent
Sendai

(10) Patent No.: US 8,130,906 B2
(45) Date of Patent: Mar. 6, 2012

(54) RADIATION IMAGING AND THERAPY APPARATUS FOR BREAST

(75) Inventor: Tomonari Sendai, Kaisei-machi (JP)

(73) Assignee: Fujifilm Corporation (JP)

( * ) Notice: Subject to any disclaimer, the term of this patent is extended or adjusted under 35 U.S.C. 154(b) by 0 days.

(21) Appl. No.: 12/558,233

(22) Filed: Sep. 11, 2009

(65) Prior Publication Data

US 2010/0074400 A1    Mar. 25, 2010

(30) Foreign Application Priority Data

Sep. 25, 2008 (JP) .................................. 2008-245672

(51) Int. Cl.
*A61N 5/10* (2006.01)
*A61B 6/04* (2006.01)
*A61B 5/05* (2006.01)

(52) U.S. Cl. ................. 378/65; 378/9; 378/37; 600/427; 600/429

(58) Field of Classification Search ................ 378/4–20, 378/37, 62, 65, 204, 205, 210; 600/425–429
See application file for complete search history.

(56) References Cited

U.S. PATENT DOCUMENTS

| | | | | |
|---|---|---|---|---|
| 5,564,438 | A * | 10/1996 | Merchant | 5/613 |
| 6,385,287 | B1 * | 5/2002 | Dorner | 378/65 |
| 6,422,748 | B1 * | 7/2002 | Shepherd et al. | 378/203 |
| 6,463,122 | B1 * | 10/2002 | Moore | 378/65 |
| 6,480,565 | B1 | 11/2002 | Ning | |
| 7,394,889 | B2 * | 7/2008 | Partain et al. | 378/37 |
| 2006/0262898 | A1 * | 11/2006 | Partain et al. | 378/37 |
| 2007/0211854 | A1 * | 9/2007 | Koshnitsky et al. | 378/65 |
| 2007/0269000 | A1 * | 11/2007 | Partain et al. | 378/37 |
| 2008/0043905 | A1 * | 2/2008 | Hassanpourgol | 378/2 |
| 2008/0317202 | A1 * | 12/2008 | Partain et al. | 378/37 |
| 2009/0080602 | A1 * | 3/2009 | Brooks et al. | 378/20 |
| 2009/0080604 | A1 * | 3/2009 | Shores et al. | 378/37 |
| 2009/0171244 | A1 * | 7/2009 | Ning et al. | 600/567 |

FOREIGN PATENT DOCUMENTS

JP    09-192245    7/1997

* cited by examiner

*Primary Examiner* — Anastasia Midkiff
(74) *Attorney, Agent, or Firm* — Studebaker & Brackett PC; Donald R. Studebaker

(57) ABSTRACT

A breast radiation imaging and therapy apparatus for performing radiation imaging of a breast and having a therapy function of applying radiation to an affected part in the breast. The apparatus includes: (i) a table formed with an opening for allowing a breast of an examinee to pass through; (ii) an imaging unit including a first radiation generating unit for applying an imaging radiation beam and a radiation detecting unit for detecting the radiation beam to output detection signals; (iii) a therapy unit including a second radiation generating unit for applying a therapeutic radiation beam, the second radiation generating unit being movable in a tangential direction of a rotational track around a rotational axis and movable in a direction substantially orthogonal to the table; and (iv) at least one rotational driving device for rotating the imaging unit and the therapy unit around the rotational axis.

20 Claims, 7 Drawing Sheets

RADIATION IMAGING AND THERAPY APPARATUS FOR BREAST

CROSS-REFERENCE TO RELATED APPLICATION

The present application claims priority from Japanese Patent Application No. 2008-245672 filed on Sep. 25, 2008, the contents of which are incorporated herein by reference in their entirety.

BACKGROUND OF THE INVENTION

1. Field of the Invention

The present invention relates to a radiation imaging and therapy apparatus for obtaining a radiation image of a breast and having a therapy function of applying radiation to an affected part in the breast.

2. Description of a Related Art

Recent years, an image-guided radiation therapy (IGRT) apparatus combining a tomographic imaging apparatus and a radiation therapy apparatus has been developed. Thereby, a radiation application method can be planned based on a three-dimensional (3D) image near an affected part, and radiation therapy for applying radiation can be performed according to the plan.

For example, Japanese Patent Application Publication JP-A-9-192245 discloses a radiation therapy system as shown in FIG. 12. The radiation therapy system includes a bed movably supported in a direction in parallel with the reference surface, an imaging apparatus (X-ray CT apparatus) that can image a part for therapy of an object to be inspected on the bed, a positioning apparatus for positioning the part for therapy from the image obtained by the imaging apparatus, and a radiation therapy apparatus for performing therapy by applying radiation to the positioned part for therapy. The imaging apparatus, the positioning apparatus, and the radiation therapy apparatus are accommodated together in one room, and a patient as the object undergoes therapy while staying on the bed because the bed sequentially moves to the locations of the respective apparatuses.

However, the image-guided radiation therapy apparatus can be used for all body organs as targets of examinations, and there is a problem that a contrast agent is necessary for an examination of breast cancer because an X-ray having high penetrating power generated by an X-ray tube voltage equal to or more than 100 kV for image formation is used. Further, since image-guided radiation therapy apparatus is used for a whole body as a target of examination, upsizing of the entire apparatus is unavoidable.

On the other hand, for the main purpose of detections and diagnoses of breast cancer, a radiation tomographic imaging apparatus for breast (mammography CT apparatus) that can obtain three-dimensional (3D) images has been developed. As an example of a mammography CT apparatus, U.S. Pat. No. 6,480,565 B1 discloses a device for producing a three-dimensional tomographic mammography image of a breast of a patient. The device disclosed in U.S. Pat. No. 6,480,565 B1 comprises: a gantry frame; at least one motor for moving the gantry frame to form a data acquisition geometry; a source of radiation attached to the gantry frame to move with the gantry frame; a flat panel detector attached to the gantry frame to move with the gantry frame, the flat panel detector being disposed in a path of the radiation; and a support on which the patient rests while the mammography projection images are taken, the support supporting the patient such that the breast is disposed between the source of radiation and the flat panel detector; the support comprising a table on which the patient lies while the mammography projection images are taken; wherein the at least one motor moves the gantry frame so that the flat panel detector takes a volume scan of the breast; and wherein the table has two breast holes for both of the patient's breasts. For imaging a tumor mass or calcification in the breast, an X-ray with high energy has a small ratio of transmission amount and the contrast of transmission image is weak, and therefore, an X-ray beam with low energy of about 25 kV to 50 kV is used.

When breast cancer detection is performed by using the device disclosed in U.S. Pat. No. 6,480,565 B 1, the patient rests face down on the table to allow two breasts to extend through the two breast holes, and one breast descends between the radiation source and the flat panel detector. The radiation source and the flat panel detector perform radiation imaging at each predetermined angular position while rotating together around a rotational axis, and thereby, the flat panel detector obtains radiation images of the breast in plural directions. The image signals obtained by the flat panel detector are transmitted to an image reconstruction and processing module. The image reconstruction and processing module three-dimensionally reconstructs the obtained radiation images to create a radiation tomographic image of the breast. Since the radiation tomographic image of the breast is a 3D image, a focus part at the rear side of the tissues such as mammary gland can be detected.

Accordingly, in the image-guided radiation therapy apparatus for performing radiation therapy for breasts, it is conceivable that the mammography CT apparatus is used in place of the imaging apparatus that can obtain radiation projection images in plural directions. However, when the mammography CT apparatus and the radiation application therapy apparatus are combined, it is difficult to reproduce the affected part location in the radiation application therapy apparatus for accurate therapy of the affected part in the breast, which has been recognized by using the mammography CT apparatus.

SUMMARY OF THE INVENTION

The present invention has been achieved in view of the above-mentioned points. A purpose of the present invention is to provide a radiation imaging and therapy apparatus for performing radiation imaging of a breast and having a therapy function of applying radiation to an affected part in the breast.

In order to accomplish the above-mentioned purpose, a radiation imaging and therapy apparatus according to one aspect of the present invention includes: (i) a table formed with an opening for allowing a breast of an examinee to pass through when the examinee lies down on the table; (ii) an imaging unit rotatable around a rotational axis, which is substantially orthogonal to the table and passes through the opening, and including a first radiation generating unit for applying an imaging radiation beam toward the breast passing through the opening of the table and a radiation detecting unit for detecting the radiation beam applied by the first radiation generating unit and transmitted through the breast to output detection signals; (iii) a therapy unit rotatable around the rotational axis, and including a second radiation generating unit for applying a therapeutic radiation beam toward the breast passing through the opening of the table, the second radiation generating unit being movable in a tangential direction of a rotational track around the rotational axis and movable in a direction substantially orthogonal to the table; and (iv) at least one rotational driving device for rotating the imaging unit and the therapy unit around the rotational axis.

According to the one aspect of the present invention, the location of a lesion within the breast can be detected based on the radiation image obtained by application of low-energy radiation from the first radiation generating unit, and high-energy therapeutic radiation is applied from the second radiation generating unit to the lesion, and therefore, the therapeutic radiation can be applied to the lesion while posture and position of a patient at detection of the location of the lesion are held.

DESCRIPTION OF THE PREFERRED EMBODIMENTS

Hereinafter, preferred embodiments of the present invention will be explained in detail with reference to the drawings. The same reference numbers are assigned to the same component elements and the description thereof will be omitted. In the following embodiments, the case where an X-ray is used as radiation will be explained, however, the present invention can be applied to cases of using α-ray, β-ray, γ-ray, electron ray, ultraviolet ray, or the like.

Figure 1:
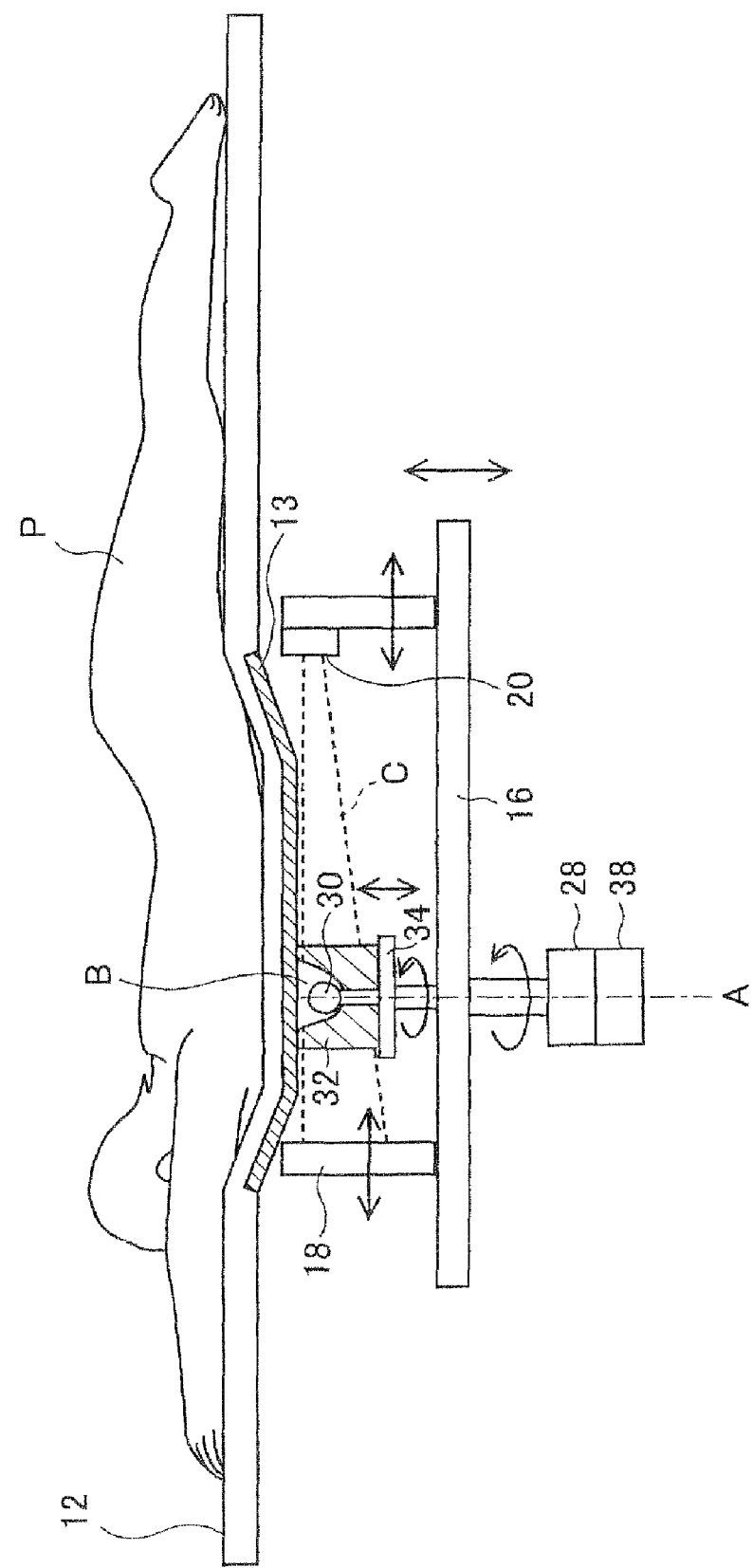
FIG. 1 is a side view showing an imaging unit and a therapy unit of a radiation imaging and therapy apparatus according to one embodiment of the present invention.

FIG. 1 is a side view showing an imaging unit and a therapy unit of a radiation imaging and therapy apparatus according to one embodiment of the present invention. As shown in FIG. 1, the radiation imaging and therapy apparatus includes a table 12 having an opening part in which an opening for passing a breast "B" of an examinee (patient) "P" is formed, an X-ray generating unit 20 for applying an imaging X-ray beam (cone beam) "C" toward the breast "B" that has passed through the opening part of the table 12, an X-ray detecting unit 18 for two-dimensionally detecting the intensity of the incident X-ray beam applied by the X-ray generating unit 20 and transmitted through the breast "B", a supporting plate 16 on which the X-ray generating unit 20 and the X-ray detecting unit 18 are mounted, a rotational driving device 28 for rotating the supporting plate 16, an X-ray generating unit 30 for applying a therapeutic X-ray beam, a beam stopper 32 for absorbing the incident X-ray beam applied by the X-ray generating unit 30 and transmitted through the breast "B", a supporting plate 34 on which the X-ray generating unit 30 and the beam stopper 32 are mounted, and a rotational driving device 38 for rotating the supporting plate 34.

Here, the X-ray generating unit 20, the X-ray detecting unit 18, and the supporting plate 16 form an imaging unit, and the X-ray generating unit 30, the beam stopper 32, and the supporting plate 34 form a therapy unit. A rotating shaft connected to the supporting plate 34 has a coaxial structure with a rotating shaft connected to the supporting plate 16. Further, an X-ray shielding plate 13 is attached to the lower surface of the table 12 for protection of the examinee "P" on the table 12 from excessive X-ray exposure. Since an X-ray beam is radiated substantially horizontally, the X-ray shielding plate 13 is provided in a part of the plate 12 projected downwards around the opening for allowing the breast "B" to pass through.

Figure 2:
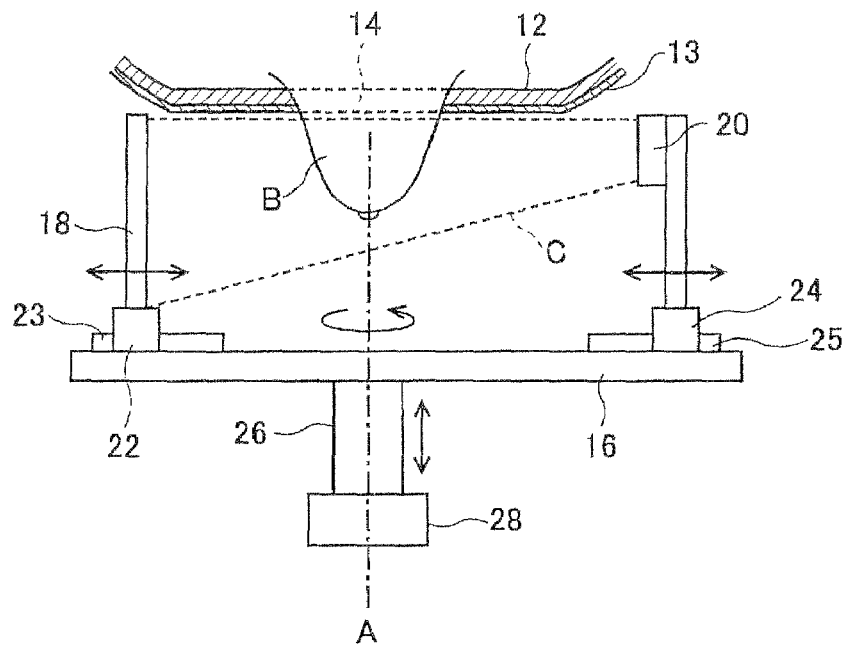
FIG. 2 is a side view showing the imaging unit of the radiation imaging and therapy apparatus according to one embodiment of the present invention.

FIG. 2 is a side view showing the imaging unit of the radiation imaging and therapy apparatus according to one embodiment of the present invention. The X-ray generating unit 20 radiates an X-ray beam having a conical shape. The X-ray detecting unit 18 has a flat panel display (FPD), on a surface of which plural X-ray detecting elements for two-dimensionally detecting the intensity of the incident X-ray beam radiated from the X-ray generating unit 20 and transmitted through the object (breast "B") are arranged. The supporting plate 16 supports the X-ray generating unit 20 and the X-ray detecting unit 18 such that the X-ray generating unit 20 and the X-ray detecting unit 18 are positioned to face each other with the rotational axis "A" in between. The rotational axis "A" is substantially orthogonal to the table 12, and passes through the opening 14.

In an imaging mode for obtaining an X-ray tomographic image of the examinee, the rotational driving device 28 rotates the supporting plate 16 around the rotational axis "A", and thereby, the X-ray generating unit 20 and the X-ray detecting unit 18 rotate around the breast "B". The X-ray generating unit 20 radiates an X-ray beam with predetermined timing, and the X-ray detecting unit 18 detects a predetermined number of X-ray transmission images (also simply referred to as "X-ray images") to output detection signals. The detection signals outputted from the X-ray detecting unit 18 are received by an imaging control unit 100 (FIG. 6), and an image signal generating unit 116 (FIG. 6) generates image signals representing the predetermined number of X-ray images based on the detection signals, and reconstructs the predetermined number of X-ray images to generate an image signal representing the X-ray tomographic image. Since it is necessary to obtain a number of X-ray images for creating an X-ray tomographic image, the X-ray beam applied from the X-ray generating unit 20 is an X-ray beam with relatively low dose for suppression of X-ray exposure of the examinee "P" and the operator.

On the supporting plate 16, an X-ray generating unit translating device 24 and an X-ray detecting unit translating device 22 are provided. The X-ray generating unit translating device 24 and the X-ray detecting unit translating device 22 translate on guide rails 25 and 23 placed toward the rotational axis "A" so as to move the X-ray generating unit 20 and the X-ray detecting unit 18 in parallel, respectively. The distance between the breast "B" and the X-ray detecting unit 18 is changed according to the size of the breast "B" as the object to adjust the image scaling factor, and thereby, the size of the image of the breast "B" can be adjusted. Further, when the breast "B" as the object is beyond the application range of the X-ray beam "C" and the imaging range of the X-ray detecting unit 18, the breast "B" can be made within the imaging range by taking the distance between the breast "B" and the X-ray generating unit 20 longer to reduce the image scaling factor. Furthermore, in the case where the rotating shaft 26 supporting the supporting plate 16 is allowed to move in the vertical direction, the end part of the breast "B" can be imaged by moving the set of the X-ray generating unit 20 and the X-ray detecting unit 18 downwards together and moving the imaging region to the end part of the breast "B".

Figure 3:
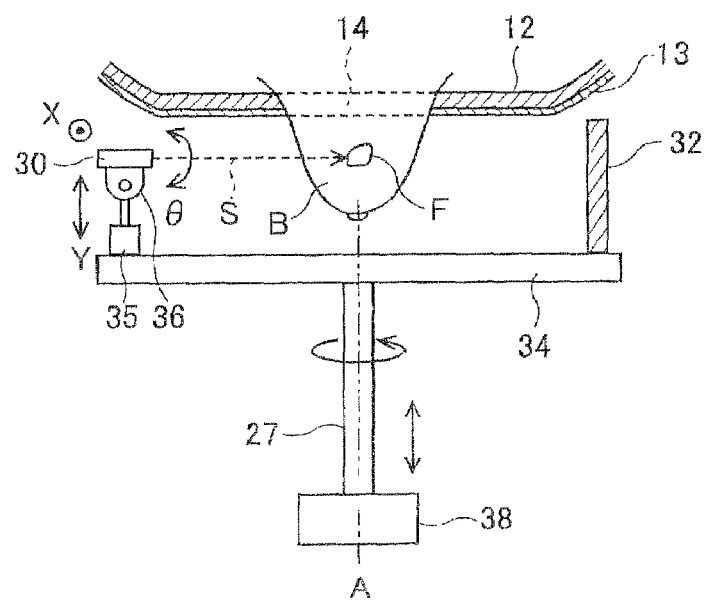
FIG. 3 is a side view showing the therapy unit of the radiation imaging and therapy apparatus according to one embodiment of the present invention.

FIG. 3 is a side view showing the therapy unit of the radiation imaging and therapy apparatus according to one embodiment of the present invention. As the X-ray generating unit 30, for example, a liniac, which will be specifically described later, is used. The x-ray generating unit 30 applies a thin X-ray beam for therapy (therapeutic beam) "S" toward an affected part (lesion) "F" in the breast "B". The beam stopper 32 absorbs the therapeutic beam "S" transmitted through the breast "B" so that the therapeutic beam "S" is not applied to persons and instruments outside. Further, the beam stopper 32 can be used as an intensity detector of an incident X-ray by being connected to an ammeter. The supporting plate 34 supports the X-ray generating unit 30 and the beam stopper 32 such that the X-ray generating unit 30 and the beam stopper 32 are positioned to face each other with the rotational axis "A" in between.

In a therapy mode for therapy of the affected part of the examinee, the rotational driving device 38 rotates the supporting plate 34 around the rotational axis "A", and thereby, the X-ray generating unit 30 and the beam stopper 32 rotate around the breast "B". The rotational axis of the supporting plate 34 is the same as the rotational axis of the supporting plate 16. The rotational driving device 38 stops rotation in a position set by an operation condition control unit 300 (FIG. 6), and the x-ray generating unit 30 applies a therapeutic X-ray beam toward the affected part "F" of the examinee.

The X-ray generating unit 30 is movable in two directions including a tangential direction of a rotational track around the rotational axis "A" (the X-axis direction in FIG. 3) and a direction substantially orthogonal to the table 12 (the Y-axis direction in FIG. 3). Thereby, the position of the X-ray generating unit 30 supported by the supporting plate 34 can be adjusted with two degrees of freedom. Furthermore, the X-ray generating unit 30 may be rotatable in the θ-axis direction (θ: azimuth angle) in FIG. 3 within a plane including the X-ray generating unit 30 and the rotational axis "A". Thereby, the direction of the X-ray generating unit 30 supported by the supporting plate 34 can be adjusted with one degree of freedom.

Figure 6:
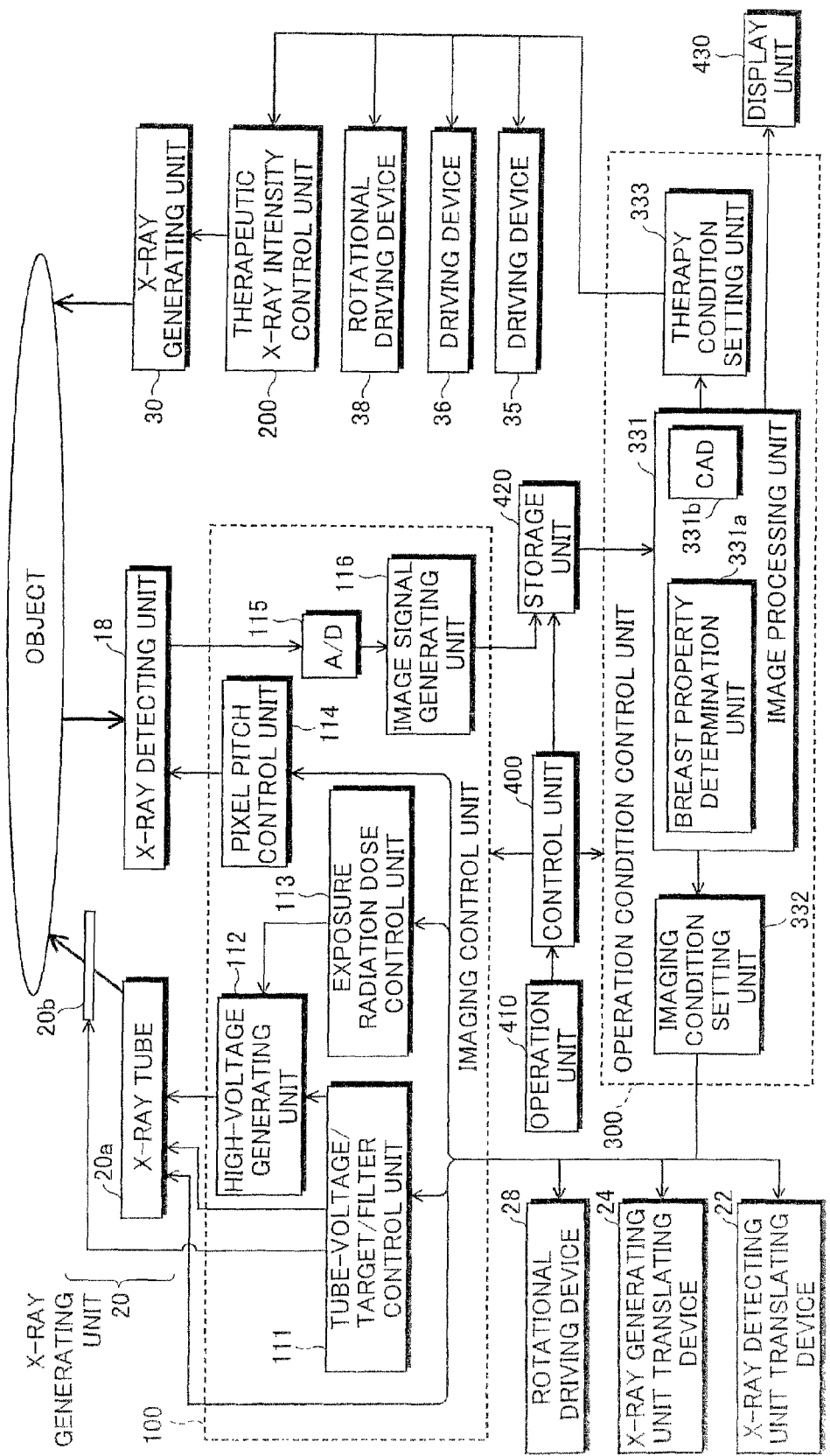
FIG. 6 is a block diagram showing a configuration of the radiation imaging and therapy apparatus according to one embodiment of the present invention.

On the supporting plate 34, a driving device 35 is provided, and a driving device 36 may be further provided. The driving device 35 moves the X-ray generating unit 30 in the X-axis direction and the Y-axis direction in FIG. 3 under the control of the operation condition control unit 300 (FIG. 6). Alternatively, the rotating shaft 27 for supporting the supporting plate 34 may be movable in the vertical direction. Further, the driving device 36 rotates the X-ray generating unit 30 in the θ-direction in FIG. 3 within the plane including the X-ray generating unit 30 and the rotational axis "A" under the control of the operation condition control unit 300. Furthermore, for easy posture control of the X-ray generating unit 30, four or more drive axes may be used.

Figure 4:
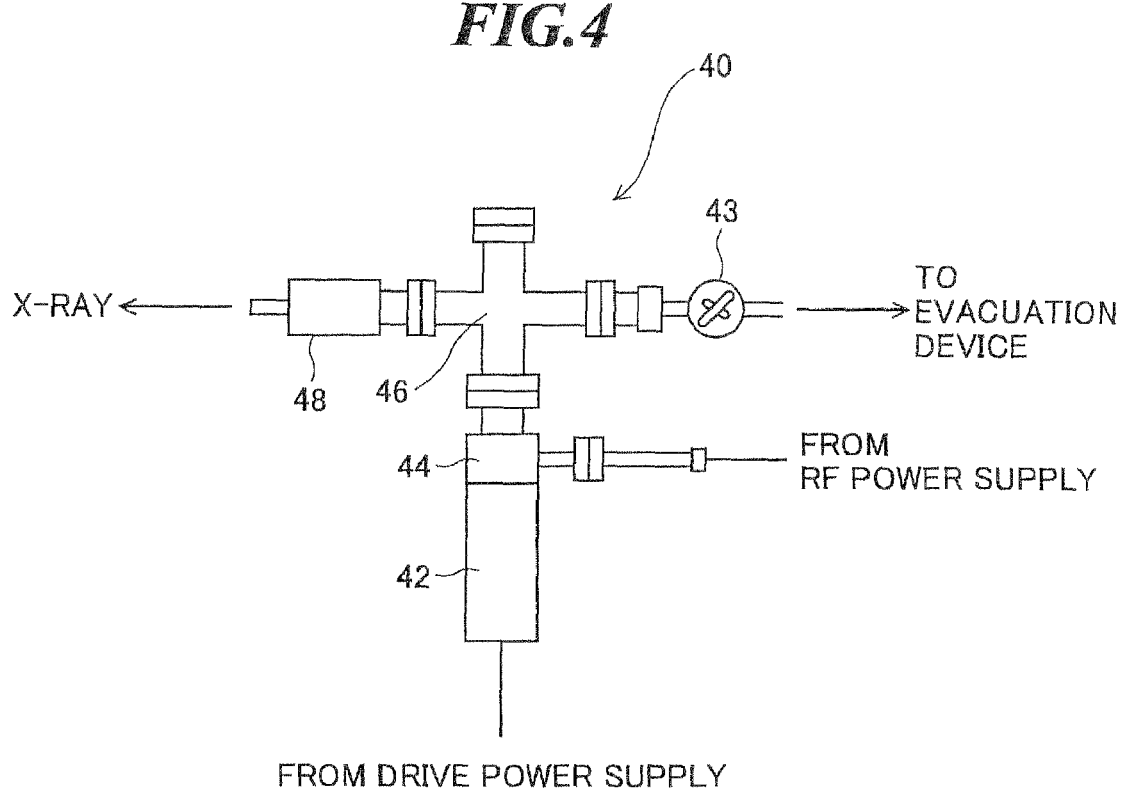
FIG. 4 shows a specific example of a liniac available for an X-ray generating unit of the therapy unit.

FIG. 4 shows a specific example of a liniac available for an X-ray generating unit of the therapy unit. A liniac 40 as shown in FIG. 4 is extremely small having a weight of about 1.5 kg and a length of about 30 cm. The liniac 40 includes an electron gun 42, an accelerating tube 44, a target part 46, an X-ray optics 48, and a vacuum valve 43 connected to an evacuation device. The electron gun 42 is supplied with a drive voltage from a drive power supply to emit electrons. The accelerating tube 44 is supplied with an RF (radio frequency) voltage from an RF power supply to accelerate the electrons emitted from the electron gun 42. The electrons accelerated by the accelerating tube 44 collide with a target in the target part 46 to emit electromagnetic waves having various energy bands. The X-ray optics 48 extracts an X-ray having a target energy band from electromagnetic waves emitted from the target part 46 to form a thin X-ray beam.

Further, a small linear-type accelerator including a standing wave-type hybrid cavity resonator having an accelerating tube length of 25 cm is also developed. Furthermore, as the X-ray generating unit 30, not limited to the liniac, but an X-ray tube using a cathode filament may be used. In the X-ray tube as well, the wavelength and intensity of an X-ray to be generated can be adjusted by selecting a metal material of an anode target or a material of an X-ray filter.

Figure 5:
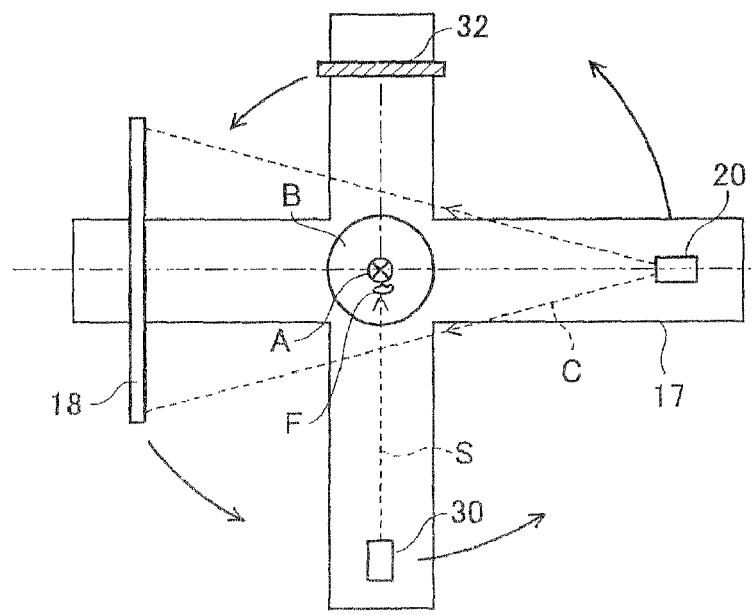
FIG. 5 is a plan view showing a positioning example of the imaging unit and the therapy unit of the radiation imaging and therapy apparatus according to one embodiment of the present invention.

FIG. 5 is a plan view showing a positioning example of the imaging unit and the therapy unit of the radiation imaging and therapy apparatus according to one embodiment of the present invention. When the imaging unit and the therapy unit are rotated together all the time, as shown in FIG. 5, the X-ray generating unit 20 and the X-ray detecting unit 18 of the imaging unit and the X-ray generating unit 30 and the beam stopper 32 of the therapy unit may be mounted on the common supporting plate 17. The X-ray generating unit 20 and the X-ray generating unit 30 may be arranged in positions in which axes of X-ray beams radiated from them are substantially orthogonal to each other.

As shown in FIG. 5, since the rotation center of the imaging unit and the rotation center of the therapy unit are aligned and the imaging unit and the therapy unit are positioned near the breast "B" as the object, the position of the target of imaging relative to the imaging unit and the position of the target of therapy relative to the therapy unit have a relatively simple relationship, and conversion of coordinates representing the positions is easy. For this purpose, the position correction data on the relationship between the positions of the X-ray generating unit 20 and the X-ray detecting unit 18 and the image scaling factor is stored in a storage unit 420 (FIG. 6). Therefore, the operation condition control unit 300 (FIG. 6) acquires the positions of the X-ray generating unit 20 and the X-ray detecting unit 18 (amounts of movement from the reference positions), and thereby, can obtain coordinates representing the actual location of the lesion based on a predetermined number (e.g., two or more) of X-ray images or one X-ray tomographic image of the breast "B". The operation condition control unit 300 controls the position and/or direction of the X-ray generating device 30 so as to apply a therapeutic X-ray beam to the lesion of the breast "B" based on the coordinates.

FIG. 6 is a block diagram showing a configuration of the radiation imaging and therapy apparatus according to one embodiment of the present invention. The radiation imaging and therapy apparatus includes an imaging control unit 100, a therapeutic X-ray intensity control unit 200, an operation condition control unit 300, a control unit 400, an operation unit 410, a storage unit 420, and a display unit 430 in addition to the component elements as shown in FIGS. 1-5. In FIG. 6, the X-ray generating unit 20 for applying an imaging X-ray beam includes an X-ray tube 20a and a filter part 20b.

The imaging control unit 100 includes a tube-voltage/target/filter control unit 111, a high-voltage generating unit 112, an exposure radiation dose control unit 113, a pixel pitch control unit 114, an analog/digital converter (A/D) 115, and an image signal generating unit 116.

The tube-voltage/target/filter control unit 111 sets the magnitude of the voltage (tube voltage) applied to the X-ray tube 20a and a combination of a material of the target to be used in the X-ray tube 20a and a material of the X-ray filter to be used in the filter part 20b (e.g., tungsten/rhodium, molybdenum/molybdenum, molybdenum/rhodium, rhodium/rhodium, or the like), and thereby, controls the characteristics of the X-ray.

The high-voltage generating unit 112 generates a voltage to be applied to the X-ray tube 20a under the control of the tube-voltage/target/filter control unit 111. The exposure radiation dose control unit 113 controls the dose of the X-ray to be applied from the X-ray tube 20a to the object. The pixel pitch control unit 114 sets a pixel pitch in the X-ray detecting unit 18. Thereby, detection signals are output at intervals set by the pixel pitch control unit 114 from plural X-ray detecting elements included in the X-ray detecting unit 18.

The analog/digital converter (A/D) 115 converts the analog detection signals outputted from the X-ray detecting unit 18 into digital detection signals. The image signal generating unit 116 generates an image signal representing an X-ray image based on the detection signals outputted from the A/D converter 115, and, when the image signals representing the predetermined number of X-ray images in plural directions obtained with respect to the object are prepared, performs reconstruction computation on the image signals to generate an image signal representing an X-ray tomographic image of the object. The image signals representing the X-ray images and the image signal representing the X-ray tomographic image generated by the image signal generating unit 116 are stored in the storage unit 420.

The operation condition control unit 300 includes an image processing unit 331, an imaging condition setting unit 332, and a therapy condition setting unit 333. The image processing unit 331 includes a breast property determination unit 331a and a CAD (computer aided detection) processing unit 331b.

The image processing unit 331 performs image processing such as linear gradation process including gain adjustment and contrast adjustment and nonlinear gradation process including γ correction on the image signals stored in the storage unit 420. Further, the image processing unit 331 outputs the image signals to the display unit 430. The display unit 430 is a raster-scan CRT display or LCD display, for example, and displays the X-ray images or the X-ray tomographic image based on the image signals.

The breast property determination unit 331a analyzes the X-ray images or the X-ray tomographic image represented by the image signals stored in the storage unit 420, and thereby, determines whether the property of the breast in the images is a dense breast or a fat breast. Further, the CAD processing unit 331b analyzes the X-ray images or the X-ray tomographic image, and thereby, detects a lesion (calcification or tumor mass) produced in the breast.

The imaging condition setting unit 332 sets conditions (the tube voltage, the combination of target/filter, the exposure radiation dose, the pixel pitch, the application direction of the X-ray beam, and so on) in the next X-ray imaging based on the analysis result of the breast property determination unit 331a and/or the CAD processing unit 331b, and controls the imaging control unit 100, the rotational driving device 28, the X-ray generating unit translating device 24, and the X-ray detecting unit translating device 22. The rotational driving device 28 outputs a signal representing the angle (the amount of rotation from the reference angle) of the supporting plate 16 or 17, the X-ray generating unit translating device 24 outputs a signal representing the position (the amount of movement from the reference position) of the X-ray generating unit 20, the X-ray detecting unit translating device 22 outputs a signal representing the position (the amount of movement from the reference position) of the X-ray detecting unit 18, and thereby, the operation condition control unit 300 can acquire the positions (the amounts of movement from the reference positions) of the X-ray generating unit 20 and the X-ray detecting unit 18.

The therapy condition setting unit 333 sets an application condition in application of a therapeutic X-ray beam performed after X-ray imaging based on the analysis result of the breast property determination unit 331a and/or the CAD processing unit 331b, and controls the therapeutic X-ray intensity control unit 200, the rotational driving device 38, and the driving device 35 and/or 36. The rotational driving device 38 outputs a signal representing the angle (the amount of rotation from the reference angle) of the supporting plate 34, the driving device 35 outputs a signal representing the position (the amount of movement from the reference position) of the X-ray generating unit 30, the driving device 36 outputs a signal representing the angle (the amount of rotation from the reference angle) of the X-ray generating unit 30, and thereby, the operation condition control unit 300 can acquire the position (the amount of movement from the reference position) and the angle (the amount of rotation from the reference angle) of the X-ray generating unit 30.

The therapeutic X-ray intensity control unit 200 adjusts the characteristic and the application dose of the therapeutic X-ray beam. The rotational driving device 38 and the driving device 35 and/or 36 adjusts the position and/or direction of the X-ray generating unit 30. Thereby, the X-ray generating unit 30 is positioned in an optimum position on the track around the breast "B", and applies an X-ray in an appropriate dose to the object.

The control unit 400 controls the respective units of the radiation imaging and therapy apparatus according to the commands and information inputted by using the operation unit 410. The operation unit 410 includes a keyboard, switch, pointing device, and an input device using the display unit 430, and is used when the operator inputs commands or information to the radiation imaging and therapy apparatus. The storage unit 420 includes a hard disk or a memory, and stores the image signals generated by the image signal generating unit 116, the position correction data on the relationship between the positions of the X-ray generating unit 20 and the X-ray detecting unit 18 and the image scaling factor, programs (software) to be used for performing various processing, information to be used for the processing, and so on.

In the embodiment, the image signal generating unit 116, the operation condition control unit 300, and the control unit 400 are configured of a central processing unit (CPU) and software for allowing the CPU to execute various kinds of processing, however, they may be configured of digital circuits or analog circuits. The software is stored in the storage unit 420. As a recording medium in the storage unit 420, not only the built-in hard disk but also a flexible disk, MO, MT, RAM, CD-ROM, DVD-ROM, or the like may be used.

Next, an operation example of the radiation imaging and therapy apparatus as shown in FIG. 6 will be explained.

The CAD processing unit 331b as shown in FIG. 6 detects the lesion in the radiation image (the predetermined number of X-ray images or the X-ray tomographic image) represented by the image signals stored in the storage unit 420, and acquires information on the positions of the X-ray generating unit 20 and the X-ray detecting unit 18, and thereby, obtains the location of the lesion by using the position correction data on the relationship between the positions of the X-ray generating unit 20 and the X-ray detecting unit 18 and the image scaling factor stored in the storage unit 420. Further, the therapy condition setting unit 333 controls the rotational driving device 38 and the driving device 35 and/or 36 such that the therapeutic radiation beam is applied from the radiation generating unit 30 toward the lesion.

Figure 7:
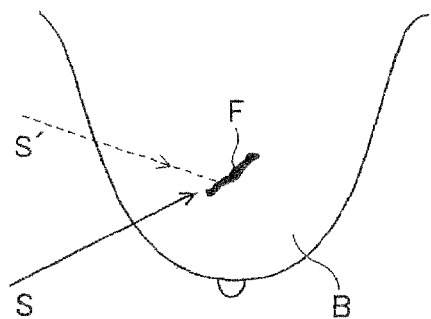
FIG. 7 is a conceptual diagram for explanation of a method of adjusting an incident direction of a therapeutic beam relative to a lesion for enhancement of effectiveness of radiation therapy.

FIG. 7 is a conceptual diagram for explanation of a method of adjusting an incident direction of a therapeutic beam relative to a lesion for enhancement of effectiveness of radiation therapy. Since the therapeutic beam "S" reaches the lesion "F" from the breast surface and attacks the cancer tissue to heal the lesion, it is desirable that the distance between the breast surface and the lesion is the minimum in a path of the therapeutic beam "S". Accordingly, in the first operation example, the therapy condition setting unit 333 computes the direction in which the distance between the breast surface and the lesion is the minimum based on the radiation images of the breast, and controls the rotational driving device 38 and the driving device 35 and/or 36 such that the therapeutic beam "S" applied from the X-ray generating unit 30 passes through the shortest distance within the breast to reach the lesion. Thereby, the rotational driving device 38 and the driving device 35 and/or 36 adjust the position and/or direction of the X-ray generating unit 30 such that the therapeutic beam "S" is applied to the lesion "F" along the direction.

Further, when the lesion is elongated as shown in FIG. 7, the therapy effect is improved further in the case where the therapeutic beam "S" enters in the longitudinal direction of the lesion "F" than in the case where the therapeutic beam "S" enters in the minor axis direction of the lesion "F". Accordingly, in the second operation example, the therapy condition setting unit 333 computes the direction in which a ratio of a length of the lesion, through which the therapeutic beam "S" is transmitted, to a length of a normal tissue, through which the therapeutic beam "S" is transmitted, is the maximum based on the radiation images of the breast, and controls the rotational driving device 38 and the driving device 35 and/or 36 such that the ratio of the length of the lesion to the length of the normal tissue is the maximum. Thereby, the rotational driving device 38 and the driving device 35 and/or 36 adjust the position and/or direction of the X-ray generating unit 30 such that the therapeutic beam "S" is applied to the lesion "F" along the direction. The therapeutic beam "S" travels in the lesion in the longitudinal direction, and thus, the adverse effect on the normal part can be minimized and the great therapy effect is expected.

Alternatively, a doctor may observe the radiation image displayed on the display unit 430, and designate a region of interest in the radiation image so as to apply the therapeutic beam "S" to the region of interest. The region of interest can be directly designated by using a pointing device such as a mouse or touch panel in the operation unit 410. Alternatively, the region of interest may be numerically designated by using a keyboard or the like in the operation unit 410. When the region of interest is designated, the therapy condition setting unit 333 controls the rotational driving device 38 and the driving device 35 and/or 36 such that the therapeutic beam "S" is applied from the X-ray generating unit 30 toward the region of interest.

Here, the CAD part 331b can determine various abnormal states in the radiation images and automatically detect lesions as candidates of the region of interest. The detected lesions may be displayed on the display part 430, and the doctor may designate the region of interest from among them. When the region of interest is designated, the therapy condition setting unit 333 controls the rotational driving device 38 and the driving device 35 and/or 36 such that the therapeutic beam "S" is applied from the X-ray generating unit 30 toward the region of interest. By providing an appropriate determination condition, the CAD part 331b can automatically determine the region of interest.

Next, a first modified example of the radiation imaging and therapy apparatus according to the one embodiment of the invention will be explained.

The X-ray generating unit typically generates an X-ray by emitting thermions from a heated cathode filament and allowing the thermions to an anode target metal. Further, the X-ray filter selectively transmits a specific X-ray. Therefore, the tube-voltage/target/filter control unit 111 as shown in FIG. 6 changes the tube voltage of the X-ray generating unit 20, the target metal, or the X-ray filter in the imaging mode and the therapy mode, and thereby, changes the energy band of the X-ray beam generated by the X-ray generating unit 20 such that the X-ray beam generated by the X-ray generating unit 20 can be used for therapy.

In this case, the imaging condition setting unit 332 as shown in FIG. 6 also plays a role of the therapy condition setting unit 333. Further, in order to prevent X-rays in unnecessary bands from entering the examinee, the tube-voltage/target/filter control unit 111 inserts an additional filter such as a bandpass filter between the X-ray tube 20a and the object in the imaging mode.

An X-ray generated by the tube voltage of 100 kV or more is used for obtaining an entire body image, however, the X-ray has too high transmittance for distinction and extraction of a tumor mass or the like in the breast. Therefore, in order to obtain a clear X-ray transmission image in X-ray tomographic imaging for breast, an X-ray generated by the tube voltage of 25 kV to 50 kV is used.

Figure 8:
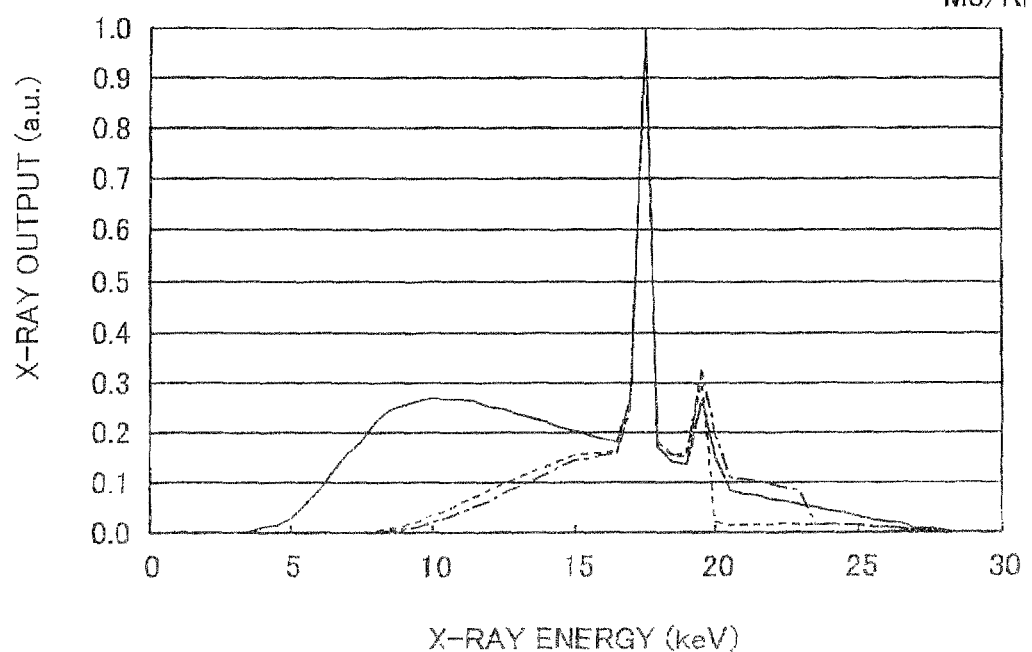
FIG. 8 shows a relationship between energy and output in an X-ray beam generated by the X-ray generating unit.

FIG. 8 shows a relationship between energy and output in an X-ray beam generated by the X-ray generating unit. In FIG. 8, the horizontal axis indicates X-ray energy (keV) and the vertical axis indicates X-ray output (a.u.). Further, FIG. 8 shows the case where molybdenum (Mo) is used as the target, and air, molybdenum (Mo) or rhodium (Rh) is used as the X-ray filter.

From FIG. 8, it is known that the maximum output is obtained near the X-ray energy of 17.5 keV (tube voltage of about 28 kV), and output reduction appears due to the X-ray filter in a range with lower X-ray energy and a range with higher X-ray energy. The X-ray causing a problem of exposure is an X-ray having relatively low energy, and accordingly, the low energy band causing the problem of exposure can be effectively removed by using an X-ray filter of molybdenum (Mo) or rhodium (Rh). Therefore, the X-ray to be used for mammography can be obtained by using molybdenum (Mo) as the target and molybdenum (Mo) or rhodium (Rh) as the X-ray filter. Further, in mammography, beryllium (Be) is used as an additional filter in the exit opening of the X-ray tube.

Figure 9:
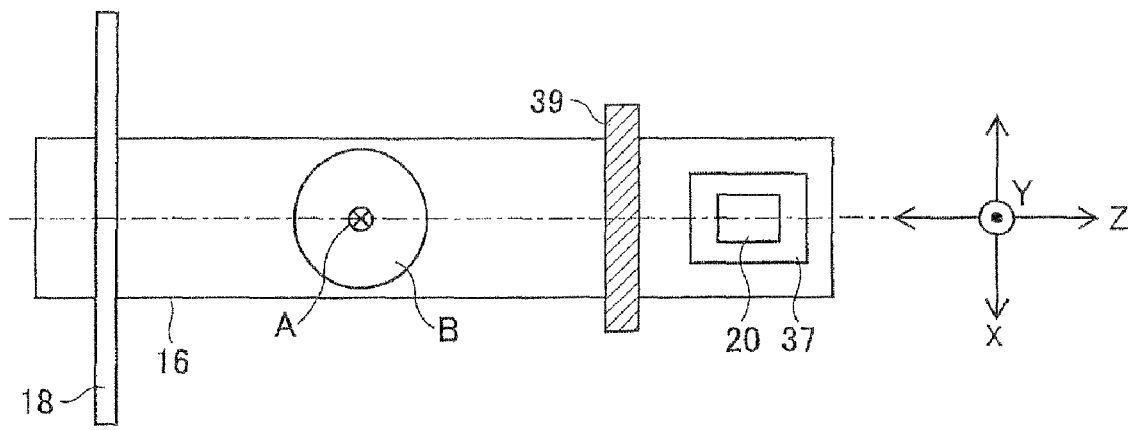
FIG. 9 shows a first modified example of the radiation imaging and therapy apparatus according to one embodiment of the present invention.

FIG. 9 shows a first modified example of the radiation imaging and therapy apparatus according to one embodiment of the present invention. As shown in FIG. 9, the X-ray generating unit 20 and the X-ray detecting unit 18 are mounted to face each other on the supporting plate 16 with the rotational axis "A" in between. The driving device 37 moves the X-ray generating unit 20 in three directions including a tangential direction of a rotational track around the rotational axis "A" (the X-axis direction in FIG. 9), a direction substantially orthogonal to the table 12 (the Y-axis direction in FIG. 9), and a direction in which a distance from the rotational axis "A" is changed (the Z-axis direction in FIG. 9) under the control of the imaging condition setting unit 332 (FIG. 6). Further, an additional filter 39 for cutting the high energy band included in the X-ray beam radiated by the X-ray generating unit 20 is retractably provided between the X-ray generating unit 20 and the breast "B" as the object.

In the imaging mode, the tube-voltage/target/filter control unit 111 (FIG. 6) inserts the additional filter 39 into an application region of the X-ray beam. While the X-ray generating unit 20, the additional filter 39, and the X-ray detecting unit 18 integrally rotate around the rotational axis "A", the X-ray generating unit 20 applies X-ray beams toward the breast "B" in predetermined periods. The high energy band included in the X-ray beam is cut by the additional filter 39, and the imaging X-ray beam is transmitted through the breast "B", enters the X-ray detecting unit 18, and forms an X-ray image.

When a lesion is discovered in the object, the process moves into the therapy mode. In the therapy mode, the rotational driving device 28 and the driving device 37 adjust the position and/or direction of the X-ray generating unit 20 under the control of the imaging condition setting unit 332. Further, the tube-voltage/target/filter control unit 111 retracts the additional filter 39 from the application region of the X-ray beam. Then, the X-ray generating unit 20 applies the therapeutic X-ray beam toward the lesion. In this manner, the obtainment of the X-ray image using the imaging X-ray beam and the therapy using the therapeutic X-ray beam can be switched by insertion and retraction of the additional filter 39.

Next, a second modified example of the radiation imaging and therapy apparatus according to the one embodiment of the invention will be explained.

Figure 10:
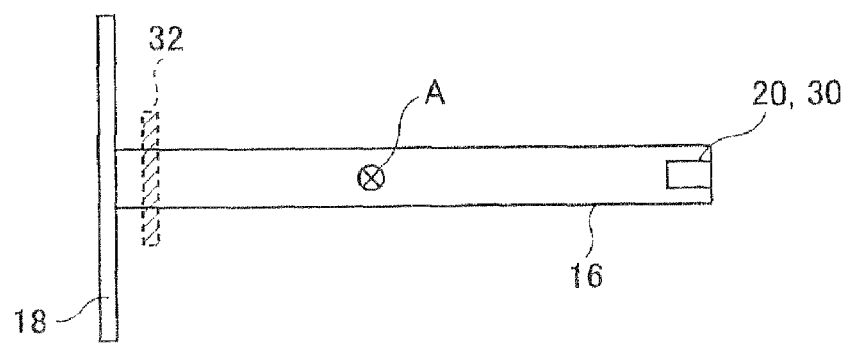
FIG. 10 shows a second modified example of the radiation imaging and therapy apparatus according to one embodiment of the present invention.

FIG. 10 shows a second modified example of the radiation imaging and therapy apparatus according to one embodiment of the present invention. In the second modified example, one of the X-ray generating unit 20 of the imaging unit and the X-ray generating unit 30 of the therapy unit is selectively mounted on the supporting plate 16.

Typically, the X-ray generating unit 30 is moved to the position where the therapeutic X-ray beam can be applied to the lesion and provides therapy after the location of the lesion is fixed after imaging, and thus, imaging and therapy are not performed at the same time. Accordingly, in the case where a lesion is discovered in the object after the object is imaged by using the X-ray generating unit 20 and the X-ray detecting unit 18 mounted on the supporting plate 16, the X-ray generating unit 20 for imaging is replaced with the X-ray generating unit 30 for therapy, and the therapeutic X-ray beam is applied toward the lesion of the object.

In the imaging mode, the regularly provided X-ray detecting unit 18 is activated, and, in the therapy mode, the beam stopper 32 is positioned in front of the X-ray detecting unit 18 for protection of the X-ray detecting unit 18. Alternatively, in the therapy mode, the X-ray detecting unit 18 may be removed when the X-ray generating unit 30 is mounted on the supporting plate 16.

Next, a third modified example of the radiation imaging and therapy apparatus according to the one embodiment of the invention will be explained.

It is known that a metal screen has a sensitization effect to an X-ray. A metal such as copper, lead, or tungsten is worked into a thin metal screen having a thickness of about 0.5 mm to 5 mm, the metal screen is provided on a front surface of a fluorescent screen including a fluorescent material, and an X-ray is applied to the metal screen, and thereby, the X-ray having energy hv produces a scattered photon having energy hv' and a Compton electron e⁻ because of interaction between the metal screen and the X-ray. The Compton electron enters the fluorescent screen with strong forward directivity, and the fluorescent screen instantaneously generates fluorescence with intensity proportional to the amount of absorbed energy. By providing a two-dimensional imaging device such as a CCD on the rear surface of the fluorescent screen, the fluorescence can be detected and an image with high sensitivity can be formed.

Figure 11:
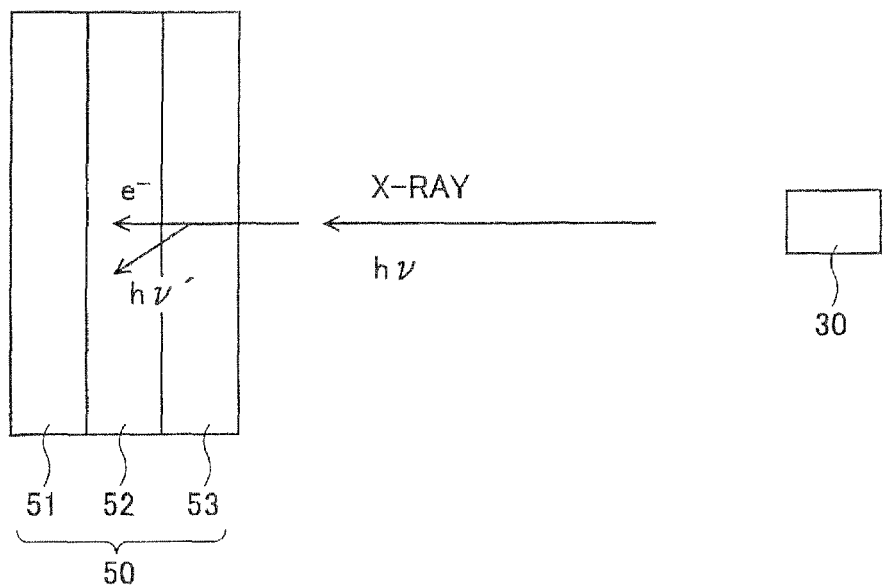
FIG. 11 shows a third modified example of the radiation imaging and therapy apparatus according to one embodiment of the present invention.
Figure 12:
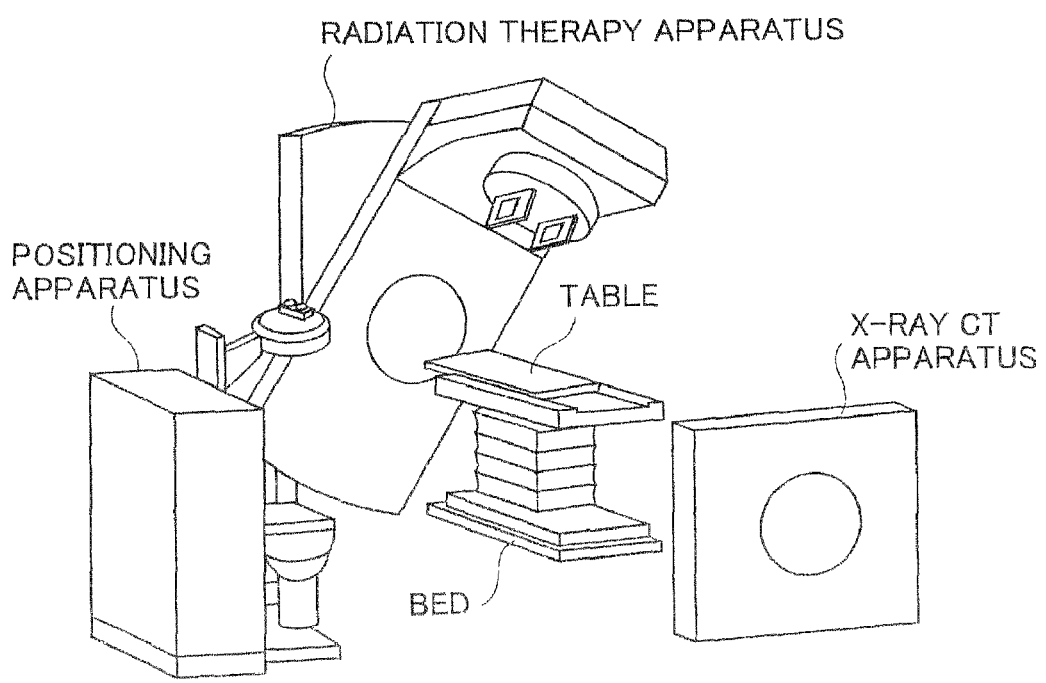
FIG. 12 shows a conventional radiation therapy system.

FIG. 11 shows a third modified example of the radiation imaging and therapy apparatus according to one embodiment of the present invention. As shown in FIG. 11, in the therapy unit, a fluorescent screen 52 is provided in front of a two-dimensional imaging device 51 such as a CCD, and a metal screen 53 is provided in front of the fluorescent screen 52, and thereby, an X-ray detecting unit 50 having a multilayer structure is provided. When a therapeutic X-ray beam is applied from the X-ray generating unit 30 to the metal screen 53, the X-ray detecting unit 50 can detect an intensity distribution of the therapeutic X-ray beam by using Compton scattering occurring in the metal screen 53. A detection result of the X-ray detecting unit 50 is outputted to the therapy condition setting unit 333, and the therapy condition setting unit 333 can adjust the intensity of the therapeutic X-ray beam based on the detection result of the X-ray detecting unit 50.

The invention claimed is:

1. A radiation imaging and therapy apparatus comprising:
   a table formed with an opening for allowing a breast of an examinee to pass through when the examinee lies down on the table;
   an imaging unit rotatable around a rotational axis, which is substantially orthogonal to said table and passes through said opening, and including a first radiation generating unit for applying an imaging radiation beam, which has a conical shape, toward the breast passing through the opening of said table and a radiation detecting unit for two-dimensionally detecting the radiation beam applied by said first radiation generating unit and transmitted through the breast to output detection signals;
   a therapy unit rotatable around the rotational axis, and including a second radiation generating unit for applying a therapeutic radiation beam, which is thinner than the imaging radiation beam, toward the breast passing through the opening of said table, said second radiation generating unit being movable in a tangential direction of a rotational track around the rotational axis and movable in a direction substantially orthogonal to said table;
   at least one rotational driving device for rotating said imaging unit and said therapy unit around the rotational axis;
   a driving device for moving said second radiation generating unit within a plane at a predetermined distance from the rotational axis;
   an image signal generating unit for generating an image signal representing one of radiation images and a radiation tomographic image based on the detection signals outputted from said radiation detecting unit; and
   an operation condition control unit for obtaining coordinates representing a location of a lesion within the breast based on one of the radiation images and the radiation tomographic image represented by the image signal generated by said image signal generating unit, and controlling said at least one rotational driving device and said driving device such that the therapeutic radiation beam is applied from said second radiation generating unit toward the lesion.

2. The radiation imaging and therapy apparatus according to claim 1, wherein said second radiation generating unit is rotatable within a plane including said second radiation generating unit and the rotational axis.

3. The radiation imaging and therapy apparatus according to claim 1, wherein said first radiation generating unit and said radiation detecting unit of said imaging unit and said second radiation generating unit of said therapy unit are mounted on a common supporting plate.

4. The radiation imaging and therapy apparatus according to claim 1,
wherein said operation condition control unit detects the lesion within the breast in one of the radiation images and the radiation tomographic image represented by the image signal generated by said image signal generating unit, and acquires information on positions of said first radiation generating unit and said radiation detecting unit, and thereby, obtains the coordinates representing the location of the lesion by using position correction data on a relationship between (i) the positions of said first radiation generating unit and said radiation detecting unit and (ii) an image scaling factor.

5. The radiation imaging and therapy apparatus according to claim 4, wherein said operation condition control unit controls said rotational driving device and said driving device such that the therapeutic radiation beam applied from said second radiation generating unit passes through the shortest distance within the breast to reach the lesion.

6. The radiation imaging and therapy apparatus according to claim 4, wherein said operation condition control unit controls said rotational driving device and said driving device such that a ratio of a length of the lesion, through which the therapeutic radiation beam is transmitted, to a length of a normal tissue, through which the therapeutic radiation beam is transmitted, is the maximum.

7. The radiation imaging and therapy apparatus according to claim 1, further comprising:
a display unit for displaying one of the radiation images and the radiation tomographic image represented by the image signal generated by said image signal generating unit; and
an operation unit to be used for designating a region of interest in the radiation images and the radiation tomographic image displayed on said display unit;
wherein said operation condition control unit controls said rotational driving device and said driving device such that the therapeutic radiation beam is applied from said second radiation generating unit toward the region of interest.

8. The radiation imaging and therapy apparatus according to claim 7, wherein said operation condition control unit includes a CAD (computer aided detection) part for automatically detecting lesions within the breast based on one of the radiation images and the radiation tomographic image, and said region of interest is designated from among the lesions detected by said CAD part.

9. The radiation imaging and therapy apparatus according to claim 1, wherein said therapy unit includes a second radiation detecting unit having a multilayer structure of an imaging device, a fluorescent screen, and a metal screen, for detecting a therapeutic radiation beam applied from said second radiation generating unit to said metal screen.

10. A radiation imaging and therapy apparatus comprising:
a table formed with an opening for allowing a breast of an examinee to pass through when the examinee lies down on the table;
a radiation generating unit for applying an imaging radiation beam in an imaging mode and a therapeutic radiation beam in a therapeutic mode toward the breast passing through the opening of said table;
an imaging control unit for changing an energy band of the imaging radiation beam and the therapeutic radiation beam applied by said radiation generating unit, and inserting a bandpass filter, which restricts the energy band of the imaging radiation beam, between said radiation generating unit and the breast in the imaging mode;
a radiation detecting unit for two-dimensionally detecting the imaging radiation beam applied by said radiation generating unit and transmitted through said bandpass filter and the breast to output detection signals;
a supporting plate for supporting said radiation generating unit and said radiation detecting unit such that said radiation generating unit and said radiation detecting unit are positioned to face with a rotational axis in between, said rotational axis being substantially orthogonal to said table and passing through said opening;
a rotational driving device for rotating said supporting plate around the rotational axis;
a driving device for moving said radiation generating unit within a plane at a predetermined distance from the rotational axis;
an image signal generating unit for generating an image signal representing one of radiation images and a radiation tomographic image based on the detection signals outputted from said radiation detecting unit; and
an operation condition control unit for obtaining coordinates representing a location of a lesion within the breast based on one of the radiation images and the radiation tomographic image represented by the image signal generated by said image signal generating unit, and controlling said rotational driving device and said driving device such that the therapeutic radiation beam is applied from said radiation generating unit toward the lesion.

11. The radiation imaging and therapy apparatus according to claim 1, wherein said second radiation generating unit includes a liniac.

12. The radiation imaging and therapy apparatus according to claim 1, wherein said second radiation generating unit includes an X-ray tube.

13. The radiation imaging and therapy apparatus according to claim 1, wherein said therapy unit further includes a beam stopper positioned to face said second radiation generating unit with the rotational axis in between.

14. The radiation imaging and therapy apparatus according to claim 13, wherein said therapy unit further includes an ammeter connected to said beam stopper, said beam stopper and said ammeter constituting a detector for detecting an intensity of an incident therapeutic radiation beam.

15. The radiation imaging and therapy apparatus according to claim 1, wherein said second radiation generating unit is rotatable in an azimuth angle direction.

16. The radiation imaging and therapy apparatus according to claim 1, wherein said first radiation generating unit and said second radiation generating unit are arranged such that an axis of the imaging radiation beam and an axis of the therapeutic radiation beam are substantially orthogonal to each other.

17. The radiation imaging and therapy apparatus according to claim 1, wherein said at least one rotational driving device includes a first rotational driving device for rotating said imaging unit around the rotational axis and a second rotational driving device for rotating said therapy unit around the rotational axis.

18. The radiation imaging and therapy apparatus according to claim 10, wherein said bandpass filter is retractably provided between said radiation generating unit and the breast.

19. The radiation imaging and therapy apparatus according to claim 10, wherein said bandpass filter cuts the energy band included in the therapeutic radiation beam.

20. The radiation imaging and therapy apparatus according to claim 10, wherein said imaging control unit includes a tube-voltage/target/filter control unit mounted on said supporting plate, for changing the energy band of the imaging radiation beam and the therapeutic radiation beam applied by said radiation generating unit, and inserting said bandpass filter between said radiation generating unit and the breast in the imaging mode.

* * * * *